United States Patent
Gilbert et al.

(10) Patent No.: US 9,532,894 B2
(45) Date of Patent: Jan. 3, 2017

(54) HIGH DENSITY ACTUATOR WITH MINIMAL LATERAL TORSION

(71) Applicant: B-TEMIA INC., Québec (CA)

(72) Inventors: Benoît Gilbert, Québec (CA); Stéphane Bédard, St-Augustin-de-Desmaures (CA)

(*) Notice: Subject to any disclaimer, the term of this patent is extended or adjusted under 35 U.S.C. 154(b) by 263 days.

(21) Appl. No.: 14/387,220

(22) PCT Filed: Mar. 21, 2013

(86) PCT No.: PCT/CA2013/000269
§ 371 (c)(1),
(2) Date: Sep. 22, 2014

(87) PCT Pub. No.: WO2013/138913
PCT Pub. Date: Sep. 26, 2013

(65) Prior Publication Data
US 2015/0051528 A1 Feb. 19, 2015

Related U.S. Application Data

(60) Provisional application No. 61/613,678, filed on Mar. 21, 2012, provisional application No. 61/642,031, filed on May 3, 2012.

(51) Int. Cl.
*A61F 5/01* (2006.01)
*A61F 2/60* (2006.01)
(Continued)

(52) U.S. Cl.
CPC ............ *A61F 5/0102* (2013.01); *A61F 2/604* (2013.01); *A61F 2/68* (2013.01); *A61F 5/01* (2013.01); *B25J 9/126* (2013.01); *B25J 17/00* (2013.01); *B25J 19/06* (2013.01); *F16D 49/08* (2013.01); *F16D 65/065* (2013.01); *F16H 35/00* (2013.01);
(Continued)

(58) Field of Classification Search
CPC ................. A61F 5/0123; A61F 5/0125; A61F 2005/0139; A61F 5/0102; A61F 2005/0167; A61F 5/0111; A61F 5/0585; A61F 5/0127; A61F 5/0195; A61F 2/54; A61F 2/60; A61F 5/01; F16D 49/10; F16D 65/06; F16D 65/18
See application file for complete search history.

(56) References Cited

U.S. PATENT DOCUMENTS 8,211,042 B2 * 7/2012 Gilbert ...................... A61F 2/64
602/16

* cited by examiner

*Primary Examiner* — Ophelia A Hawthorne
(74) *Attorney, Agent, or Firm* — Equinox IP; Christian Robillard

(57) ABSTRACT

A high density actuator, comprising a housing assembly composed of a first housing element containing a motor stator and a second housing element containing a gear reduction mechanism, a rotational core positioned at the center of the housing assembly, the rotational core being composed of a motor rotor and a transmission input operatively connected to the motor rotor, a transmission output positioned between the transmission input and the housing assembly, the transmission output forming an actuator output, a torque transfer output operatively connected to the actuator output and a center shaft connected to the torque transfer output in its center and in rotational contact with the first housing element, the center shaft passing through the transmission output, rotational core and second housing element to ensure proper radial and axial alignment.

20 Claims, 6 Drawing Sheets

(51) Int. Cl.
*A61F 2/68* (2006.01)
*F16D 49/08* (2006.01)
*F16D 65/06* (2006.01)
*B25J 9/12* (2006.01)
*B25J 17/00* (2006.01)
*B25J 19/06* (2006.01)
*F16H 35/00* (2006.01)
*F16H 57/02* (2012.01)
*A61F 2/50* (2006.01)
*A61F 2/70* (2006.01)
*A61F 2/76* (2006.01)
*F16D 121/14* (2012.01)
*F16D 125/28* (2012.01)

(52) U.S. Cl.
CPC ......... *F16H 57/02* (2013.01); *A61F 2002/503* (2013.01); *A61F 2002/6818* (2013.01); *A61F 2002/6845* (2013.01); *A61F 2002/6863* (2013.01); *A61F 2002/701* (2013.01); *A61F 2002/7645* (2013.01); *A61F 2005/0158* (2013.01); *A61F 2005/0165* (2013.01); *A61F 2005/0169* (2013.01); *A61F 2250/0074* (2013.01); *F16D 2121/14* (2013.01); *F16D 2125/28* (2013.01); *Y10S 901/23* (2013.01); *Y10S 901/27* (2013.01); *Y10S 901/46* (2013.01); *Y10T 74/2186* (2015.01)

HIGH DENSITY ACTUATOR WITH MINIMAL LATERAL TORSION

CROSS-REFERENCE TO RELATED APPLICATIONS

This application claims the benefits of U.S. provisional patent applications Nos. 61/613,678 and 61/642,031, filed on Mar. 21, 2012 and May 3, 2012, respectively, which are herein incorporated by reference.

TECHNICAL FIELD

The present disclosure relates to a high density actuator with minimal lateral torsion.

BACKGROUND

Typical actuators have poor torque density (by volume or weight) partly because they require extra hardware (bearings, levers, pivots . . . ) to support the main elements (motor, transmission).

For example, a linear actuator (motor and ball-screw) requires a lever and bearings to convert the linear motion into rotational motion. Although highly energy-efficient, this arrangement is typically bulky and heavy.

Another example is the rotational actuator (motor and in-axis transmission) requires an output stage bearing to support loads. This bearing is typically located axially on the actuator or on the outer diameter, which can significantly increase the size and weight of the actuator.

Furthermore, robotic actuators require protection for over torque conditions. The solution to this typically consists in a slip clutch or other similar device. Consequently, commercial versions of such devices are cumbersome and heavy.

Accordingly, there is a need for a lighter and more compact actuator.

SUMMARY

A high density actuator, comprising:
a housing assembly composed of:
   a first housing element containing a motor stator;
   a second housing element containing a gear reduction mechanism;
a rotational core positioned at the center of the housing assembly, the rotational core being composed of:
   a motor rotor;
   a transmission input operatively connected to the motor rotor;
a transmission output positioned between the transmission input and the housing assembly, the transmission output forming an actuator output;
a torque transfer output operatively connected to the actuator output; and
a center shaft connected to the torque transfer output in its center and in rotational contact with the first housing element, the center shaft passing through the transmission output, rotational core and second housing element;
wherein the center shaft ensures proper radial and axial alignment between the housing assembly and the torque transfer output.

There is also provided a high density actuator as described above, wherein the transmission output is operatively connected between the transmission input and the gear reduction mechanism through an opening of the second housing element.

There is further provided a high density actuator as described above, further comprising conical roller bearings positioned between the center shaft and the first housing element.

There is also provided a high density actuator as described above, wherein the center shaft comprises a threaded portion screwed into the torque transfer output and a non-threaded portion press-fitted within the torque transfer output.

There is further provided a high density actuator as described above, further comprising a torque sensor for measuring a torque applied by the high density actuator, for example a flexible sensor beam having a first extremity connected to the housing assembly and a sensor magnet positioned on the housing assembly, wherein displacement of a second extremity of the flexible sensor beam relative to the housing assembly measured by the sensor magnet is indicative of the torque applied by the high density actuator.

There is still further provided a high density actuator as described above, further comprising an angle sensor for measuring a displacement of the output of the transmission with respect to the input of the transmission, for example a sensor reader positioned on the housing assembly and a sensor magnet positioned on a support shaft passing through the center shaft.

There is also further provided a high density actuator as described above, wherein the transmission input is a wave generator, the gear reduction mechanism is a circular spline and the transmission output is a flex spline forming a harmonic drive.

There is also provided a high density actuator as described above, further comprising a torque limiting assembly positioned around the torque transfer output configured to frictionally engage or disengage the brake pad and the band with the torque transfer output, and in an embodiment comprises a tension adjustment mechanism configured so as to augment or diminish the frictional engagement of the brake pad and the band with the torque transfer output.

There is further provided an actuated orthothic device, comprising:
   a proximal and a brace structures for attachment to a limb of a user; and
   a high density actuator as described above operatively connected to the proximal and the distal brace structures to impart movement to the limb of the user;
wherein the housing assembly is connected to the proximal structure and the distal brace structures and the torque transfer output is connected to the proximal distal brace structure.

BRIEF DESCRIPTION OF THE FIGURES

Embodiments of the disclosure will be described by way of examples only with reference to the accompanying drawings, in which.

DETAILED DESCRIPTION

Generally stated, the non-limitative illustrative embodiment of the present disclosure provides a high density actuator with minimal lateral torsion consisting in a compact arrangement of a brushless motor, a single-stage transmission (50:1 ratio for the illustrative embodiment), an over torque protection mechanism and a torque sensor. The transmission is located axially relative to the motor, and the output stage bearing (providing strength and stiffness when external loads are applied) is located concentric to the motor (inwards), thus saving space and weight. The output stage bearing consists in a set of conical bearings in "O" arrangement. Furthermore, the actuator angle sensor reference shaft is positioned in the center of all those elements, saving even more space. The over-torque mechanism, which can be manually decoupled, consists in custom slip clutch located around the output element of the transmission, providing again a very compact arrangement. The torque sensor is used to measure the output torque. In the illustrative embodiment, the torque sensor consists in a magnetic micrometer-range sensor that measures the deflection of a flexible beam located on the outside of the actuator.

Figure 1:
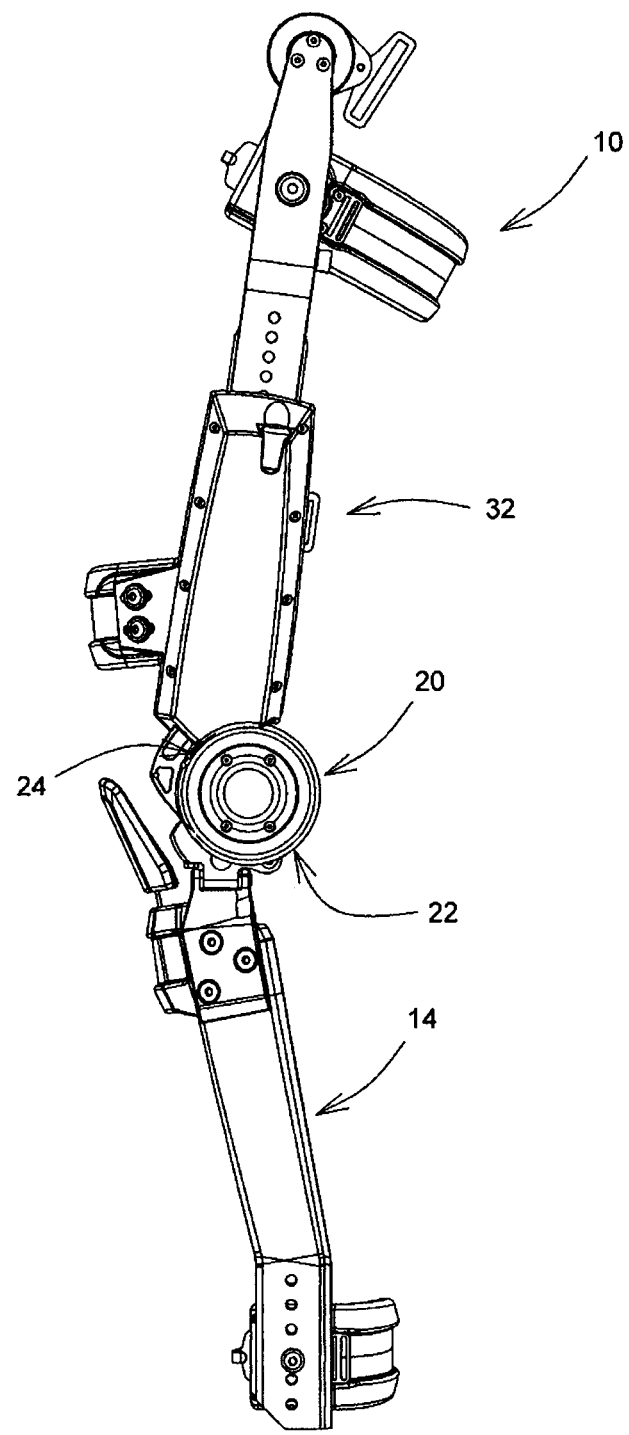
FIG. 1 is a side view of an actuated orthotic device integrating the high density actuator.

Referring to FIG. 1, there is shown an illustrative example of the high density actuator 20 integrated into an actuated orthotic device 10 having proximal 12 and distal 14 brace structures for attachment to the limb of a user. The proximal 12 and distal 14 brace structures are operatively linked together via the high density actuator 20 which imparts movement to the limb of the user.

Figure 2:
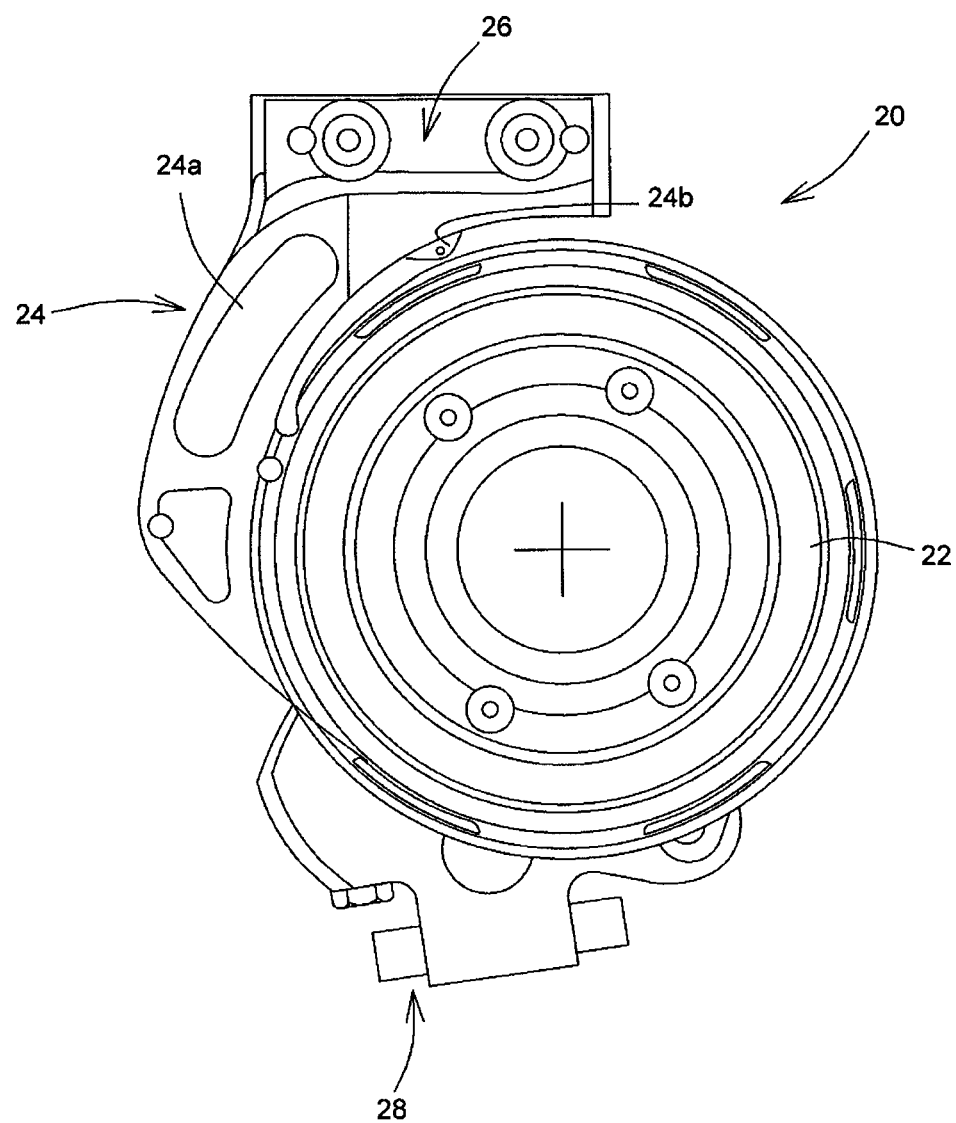
FIG. 2 is a side view of the high density actuator in accordance with an illustrative embodiment of the present disclosure.

Referring to FIG. 2, the high density actuator 20 generally comprises a housing assembly 22 that protects its internal components, which will be disclosed further below, a torque sensor 24 comprising a torque sensor beam 24a supporting proximal connector 26 thereon for connecting to the proximal brace structure 12 and a torque sensor magnet 24b, and a distal connector 28 for connecting to the distal brace structure 14. The proximal 12 and distal 14 brace structures can rotate relative to one another within about 160 degrees. The rotation limits are determined by a mechanical stop in extension and by the interference between the user's upper and lower limb in flexion, for example the upper and lower leg.

Figure 3:
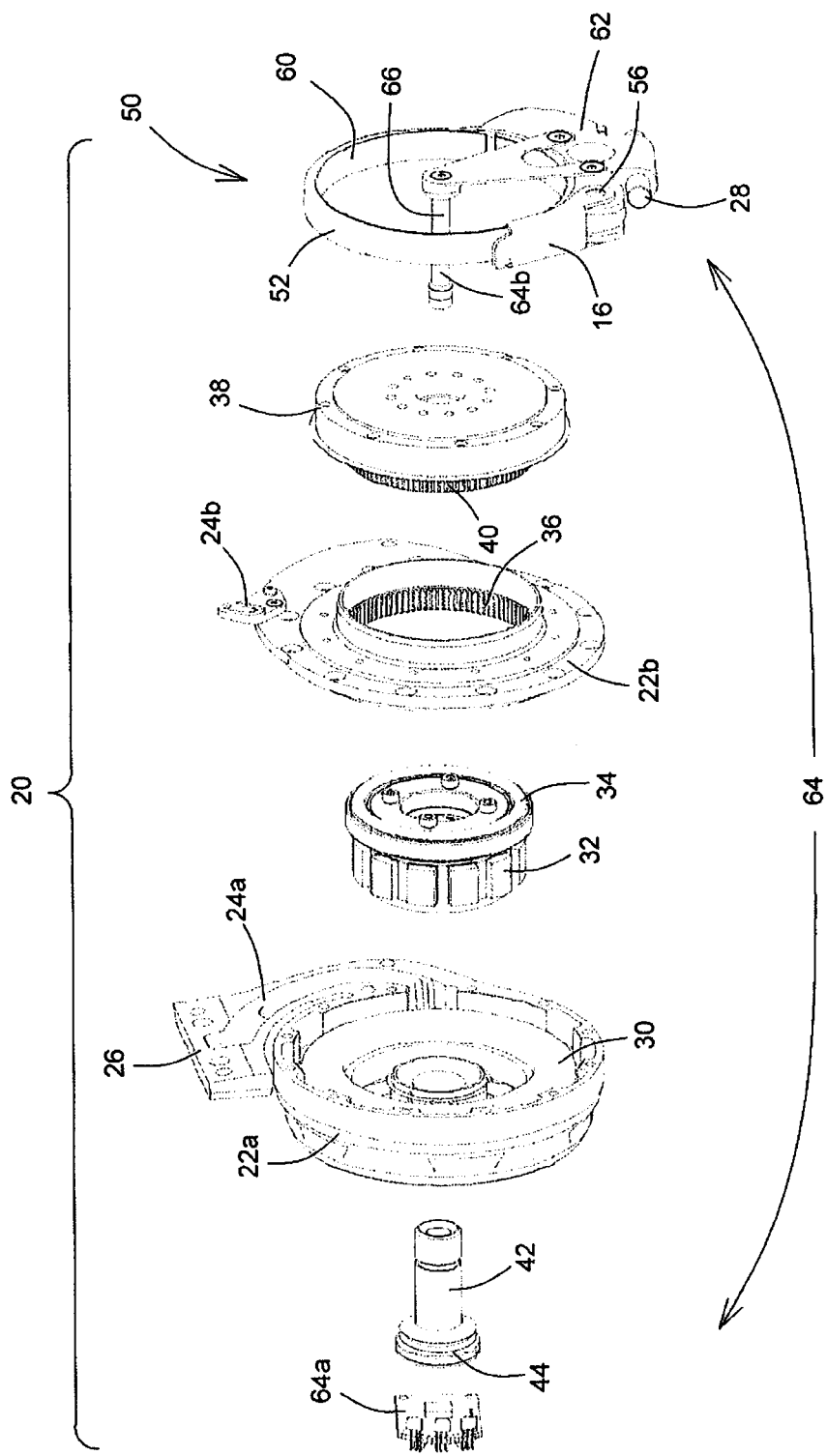
FIG. 3 is an exploded perspective view of the high density actuator of FIG. 2.

Referring now to FIG. 3, the housing assembly 22, formed of housing elements 22a and 22b, encloses a brushless DC motor (for example an Emoteq HT03000 motor though is to be understood that the motor selection may vary depending on the application), transmission elements and sensors, namely the torque sensor beam 24a, the torque sensor magnet 24b, the motor stator 30 and rotor 32, the transmission input 34, the gear reduction mechanism 36, the torque transfer output 38, for example a rotating drum or shaft, with transmission output 40, the center shaft 42 with conical roller bearings 44, and the angle sensor 64 composed of angle sensor reader 64a and angle sensor magnet 64b. In the present illustrative embodiment, the high density actuator 20 further comprises a torque limiting clutch 50. It is to be understood that in alternative embodiments other torque sensors (for example load cells, strain gauges, thin beam load cells, high accuracy linear optical sensors, etc.) and/or angle sensors (for example hall sensors, absolute position optical disks, resolvers, potentiometers, etc.) could be used.

In the illustrative embodiment, the transmission input 34, the gear reduction mechanism 36 and transmission output 40 form a harmonic drive with a transmission ratio of 50:1 with the transmission input 34 being in the form of a wave generator, the gear reduction mechanism 36 a circular spline and the transmission output 40 a flex spline. It is to be understood that the transmission ratio may vary depending on the application and/or motor used. The motor rotor 32 is connected to the transmission input 34, which can freely rotate via the set of conical roller bearings 44 on center shaft 42. When a current is applied to the motor stator 30, the rotational core (i.e. the motor rotor 32 and transmission input 34), the transmission output 40 and torque transfer output 38 rotate. This rotation causes the torque transfer output 38 to rotate the equivalent of 1 turn for every 50 rotations of the motor rotor 32.

Figure 4:
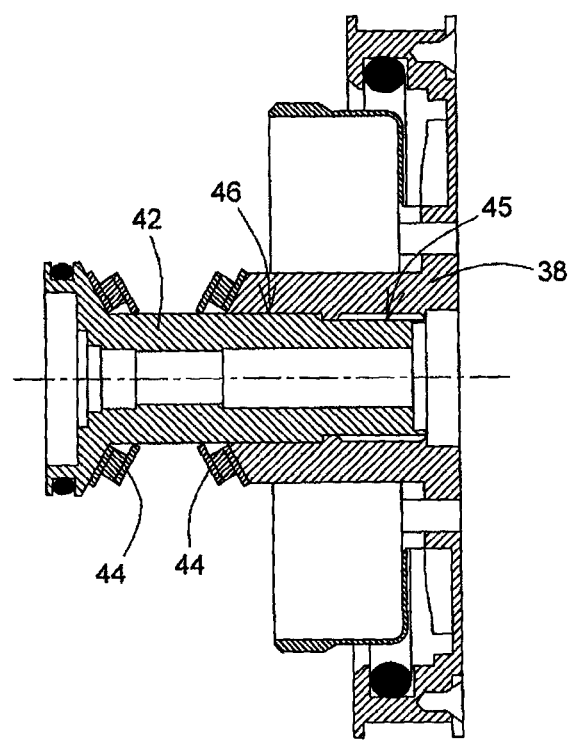
FIG. 4 is a cross-sectional view of the center shaft fitted into the torque transfer output.

The center shaft 42 and its set of conical roller bearings 44 ensure the proper radial and axial alignment between the housing assembly 22, the motor rotor 32, the transmission input 34, the transmission output 40 and the torque transfer output 38. Referring to FIG. 4, the center shaft 42 includes a threaded 45 and non-threaded portions 46, the threaded portion 45 screws into the torque transfer output 38 while the concentricity is ensured by a slight press-fit between the non-threaded portion 46 and the torque transfer output 38. Using a set of conical roller bearings 44 provides the basic characteristics of more traditional angle-contact ball bearings in "O" arrangement, but is stiffer and more compact. The fact that the conical roller bearings 44 do not have traditional raceways—that require a bore and a shaft for installation—allow for a radially smaller assembly. The radial dimension is critical since the bearing needs to fit inside the motor. An example of conical roller bearings 44 could be three superimposed conical structures with the middle conical structure having therein radially extending cylindrical rollers protruding from each side of the middle conical structure, allowing the other two conical structures to freely rotate.

The angle sensor reader 64a, positioned on housing element 22a, works in conjunction with the angle sensor magnet 64b to determine the absolute angle between the proximal 26 and distal 28 connectors. The angle sensor 64 provides a position feedback of the motor rotor 32 to a motor controller (i.e. motor drive). The angle sensor magnet 64b is held in place by a small diameter support shaft 66 that passes through the center shaft 42.

This concentric arrangement of the support shaft 66, the center shaft 42 with conical roller bearings 44 and the stacking of the motor rotor 32, the transmission input 34, the transmission output 40 and the torque transfer output 38 allows for the highly compact design of the high density actuator 20.

The torque sensor beam 24a consists in a flexible member that protrudes from the housing assembly 22. The torque sensor 24 is designed to evaluate the torque applied on the high density actuator 20 based on the actual deformation of the flexible member (i.e. torque sensor beam 24a). The torque sensor 24 is a magnetic linear displacement sensor that measures the travel of the extremity of the torque sensor beam 24a relative to the housing assembly 22, on which is positioned the torque sensor magnet 24b. The torque sensor 24 provides readings through the complete range of expected torque levels. In the illustrative embodiment, the torque sensor 24 readings range is from −50 Nm to +50 Nm. However, the torque sensor 24 must also provide readouts for torque levels exceeding those values in order to allow for good torque controllability (i.e. without signal saturation) as well as for peak force detection for system protection.

An example of a sensor that can be used for the torque sensor 24 is the AustriaMicroSystems AS5311, which has a resolution of 0.488 microns (12 bits over 2 mm).

Traditionally, strain gauges are used in lieu of displacement sensors to accurately measure forces and torques. The main disadvantages of strain gauges are the following:
- Installation requires high precision.
- Can easily be affected by stresses in directions other than the one being measured.
- Sensitivity to electromagnetic noise.
- Sensitivity to temperature variations.
- Requires a high fidelity temperature compensated measuring circuit.
- Requires individual calibration.

The torque sensor 24 addresses all of these inconvenient, namely:
- Easy to install.
- Measures deformation in a single axis without being affected by efforts in other directions.
- No sensitivity to electromagnetic noise (uses digital communication).
- No sensitivity to temperature variations.
- Does not require high fidelity temperature compensated measuring circuit.
- Does not require individual calibration.

Torque Limiting Clutch

In its illustrative embodiment, the high density actuator 20 is provided with a torque limiting clutch 50 which consists of a band brake mechanism that starts slipping when the torque is higher than the preset torque. It behaves the same way as a torque limiting clutch and has the same primary goals, namely:
- Protect the high density actuator 20 (the motor rotor 32, the transmission input 34, the gear reduction mechanism 36, the transmission output 40, the torque transfer output 38 and other mechanical components) from external high impact shocks.
- Protect the high density actuator 20 from inertial loads when the high density actuator 20 is hitting a travel extension limit (hard stop) at high speed. In this case extreme loads would occur if the kinetic energy was not dissipated somewhere.
- Protect the environment from high forces that could be exerted by the high density actuator 20.

Figure 5:
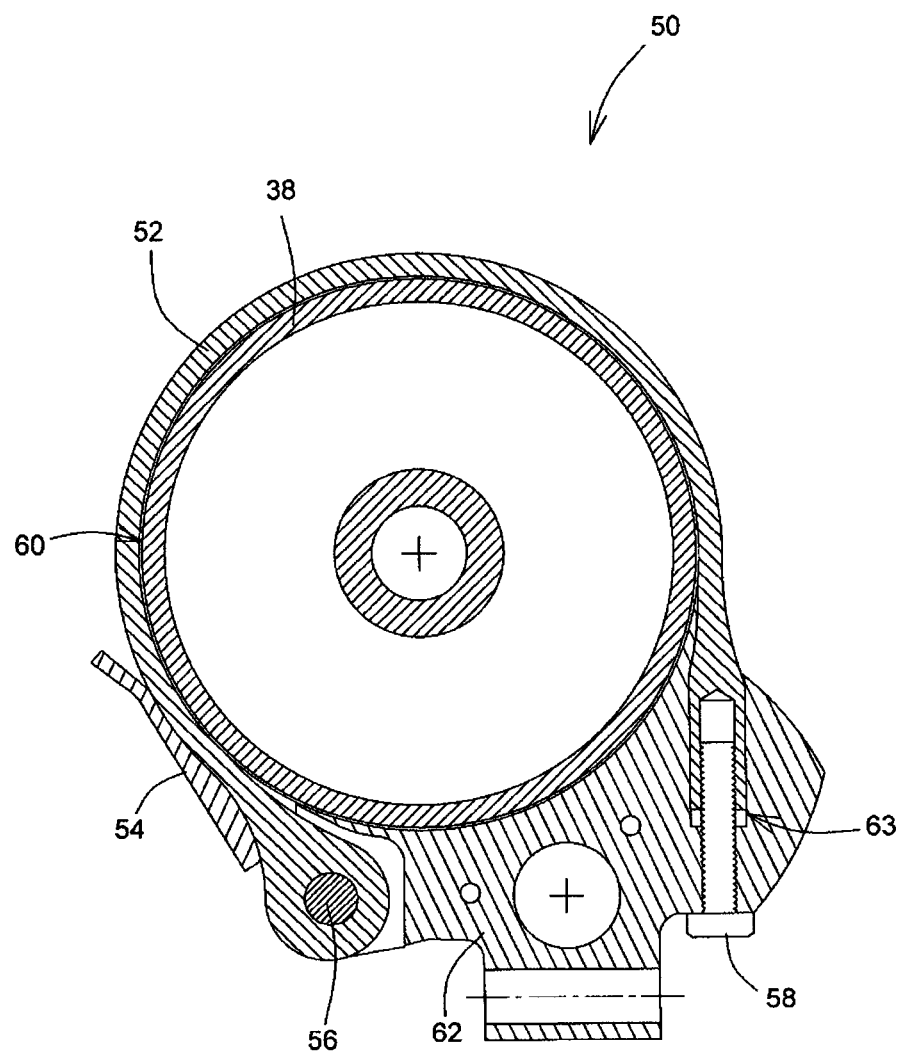
FIG. 5 is a cross-sectional view of the torque limiting clutch.
Figure 6:
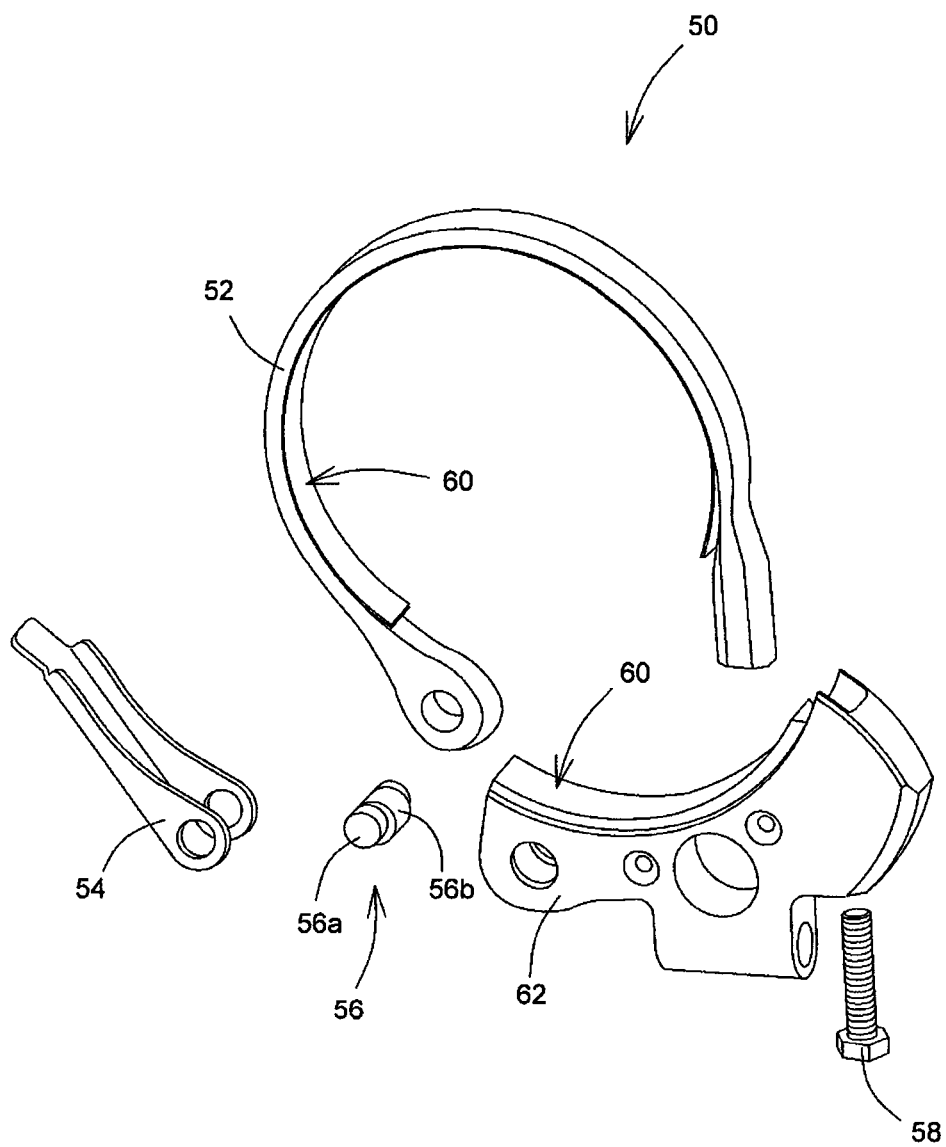
FIG. 6 is an exploded view of the torque limiting clutch components.

Referring to FIGS. 3, 5 and 6, the torque limiting clutch 50 consists of a band 52 that is wrapped partly around the torque transfer output 38 of the high density actuator 20 and a brake pad 62. Tension can be applied to the band 52 using, for example, a lever 54 attached to a cam 56 linking the band 52 to a first extremity of the brake pad 62. It is to be understood that mechanisms other than lever 54 may be used to operate the cam 56. The tension can be adjusted using a tension adjustment mechanism here in the form of a screw 58 operatively connecting the band 52 to a second extremity of the brake pad 62, wherein rotation of the crew 58 in a first direction pulls the band 52 into a cavity 63 within the brake pad 62, therefore augmenting the frictional engagement of the brake pad 62 and the band 52 with the torque transfer output 38, and rotation in the opposed direction allows the band 52 to pull out of the cavity 63, therefore diminishing the frictional engagement of the brake pad 62 and the band 52 with the torque transfer output 38. A liner 60, for example made of a high friction material, serves as a friction surface. The liner 60 is advantageously wear resistant and somewhat soft or compressible in order to "encapsulate" any dirt or particles that may be trapped between the band 52, the brake pad 62 and the torque transfer output 38. The band 52, the brake pad 62 and the torque transfer output 38 are advantageously made from the same material, for example Alu 7075-T6, to ensure that the braking force does not change significantly when the temperature fluctuates due to, for example, thermal expansion. The torque transfer output 38 may be, for example, hard anodized (i.e. type II, 50 µm) for wear resistance.

The torque limiting clutch 50 can be disengaged, for example by lifting lever 54, positioning the cam 56 in a position that allows for completely free motion of the torque transfer output 38. The torque limiting clutch 50 can be disengaged in case of, for example, malfunction of the high density actuator 20 or power failure.

The cam 56 provides the tension in the band 52 when the lever 54 is engaged. The cam 56 is designed with two eccentric bearing surfaces 56a and 56b (best seen in FIG. 6) that are off center with regard to one another. After assembly, the lever 54 is advantageously micro-welded onto the cam 56 thus making them unitary. The tension adjustment mechanism, i.e. screw 58, is used to adjust the band 52 tension in order to get the desired braking torque.

As mentioned previously, the angle sensor magnet 64b is mounted on shaft 66 supported by the brake pad 62. The brake pad 62 being configured to be connected to the distal brace structure 14, the angle sensor magnet 64b and the angle sensor reader 64a cooperate together in order to provide a measure of the angle between the proximal 12 and distal 14 brace structures.

In an alternative embodiment, the torque limiting clutch 50 may be replaced by another mechanism that limits the torque by slipping (as in a friction plate slip-clutch) or uncoupling the load entirely (as in a shear pin). In a further embodiment, the torque limiting clutch 50 may be omitted, in which case a position sensor is required and the distal connector 28 linked to the torque transfer output 38. However, this embodiment is subject to the risk of damaging the high density actuator 20 or the environment when subject to high impact shocks, extreme loads or high forces.

It is further to be understood that the high density actuator may be adapted for applications other than orthotic and prosthetic devices without departing from the scope of the present disclosure.

Although the present disclosure has been described with a certain degree of particularity and by way of an illustrative embodiments and examples thereof, it is to be understood that the present disclosure is not limited to the features of the embodiments described and illustrated herein, but includes all variations and modifications within the scope and spirit of the disclosure as hereinafter claimed.

What is claimed is:
1. A high density actuator (20), comprising:
  a housing assembly (22) composed of:
    a first housing element (22a) containing a motor stator (30);
    a second housing element (22b) containing a gear reduction mechanism (36);
  a rotational core (32, 34) positioned at the center of the housing assembly (22), the rotational core (32, 34) being composed of:
    a motor rotor (32);
    a transmission input (34) operatively connected to the motor rotor (32);

a transmission output (40) positioned between the transmission input (34) and the housing assembly (22), the transmission output (40) forming an actuator output (40);

a torque transfer output (38) operatively connected to the actuator output (40); and a center shaft (42) connected to the torque transfer output (38) in its center and in rotational contact with the first housing element (22a), the center shaft (42) passing through the transmission output (40), rotational core (32, 34) and second housing element (22b);

wherein the center shaft (42) ensures proper radial and axial alignment between the housing assembly (22) and the torque transfer output (38).

2. The high density actuator (20) of claim 1, further comprising a torque limiting assembly (50) comprising:

a brake pad (62);

a band (52) connected at a first end to a first end of the brake pad (62); and a cam (56) linking a second end of the band (52) to a second end of the brake pad (62);

wherein the brake pad (62) and the band (52) are connected to the housing assembly (22) and positioned around the torque transfer output (38), whereby the positioning of the cam (56) in a first position frictionally engages the brake pad (62) and the band (52) with the torque transfer output (38), and positioning of the cam (56) in a second position disengages the brake pad (62) and the band (52) with the torque transfer output (38).

3. The high density actuator (20) of claim 2, wherein the torque limiting assembly (50) further comprises a tension adjustment mechanism (58) connecting the first end of the band (52) to the first end of the brake pad (62), wherein the tension adjustment mechanism (58) is configured so as to augment or diminish the frictional engagement of the brake pad (62) and the band (52) with the torque transfer output (38) when the cam (56) is in the first position.

4. The high density actuator (20) of claim 2, wherein the torque limiting assembly (50) further comprises a liner (60) positioned on a surface of the band (52) and the brake pad (62) that is in frictional engagement with the torque transfer output (38) when the cam (56) is in the first position.

5. The high density actuator (20) of claim 2, wherein the cam (56) is composed of two eccentric baring surfaces (56a, 56b) off center with regard to one another.

6. The high density actuator (20) of claim 2, wherein the torque transfer output (38) is a rotating drum.

7. The high density actuator (20) of claim 1, further comprising a torque sensor (24) for measuring a torque applied by the high density actuator (20).

8. The high density actuator (20) of claim 7, wherein the torque sensor (24) comprises a flexible sensor beam (24a) having a first extremity connected to the housing assembly (22) and a sensor magnet (24b) positioned on the housing assembly (22), wherein displacement of a second extremity of the flexible sensor beam (24a) relative to the housing assembly (22) measured by the sensor magnet (24b) is indicative of the torque applied by the high density actuator (20).

9. The high density actuator (20) of claim 1, further comprising an angle sensor (64) for measuring a displacement of the transmission output (40) with respect to the transmission input (34).

10. The high density actuator (20) of claim 9, wherein the angle sensor (64) comprises a sensor reader (64a) positioned on the housing assembly (22) and a sensor magnet (64b) positioned on a support shaft (66) passing through the center shaft (42).

11. The high density actuator (20) of claim 1, wherein the transmission output (40) is operatively connected between the transmission input (34) and the gear reduction mechanism (36) through an opening of the second housing element (22b).

12. The high density actuator (20) of claim 1, further comprising conical roller bearings (44) positioned between the center shaft (42) and the first housing element (22a).

13. The high density actuator (20) of claim 1, wherein the center shaft (42) comprises a threaded portion (45) screwed into the torque transfer output (38) and a non-threaded portion (46) press-fitted within the torque transfer output (38).

14. The high density actuator (20) of claim 1, wherein the transmission input (34) is a wave generator, the gear reduction mechanism (36) is a circular spline and the transmission output (40) is a flex spline forming a harmonic drive.

15. An actuated orthothic device (10), comprising:

a proximal (12) and a distal (14) brace structures for attachment to a limb of a user; and a high density actuator (20) in accordance with claim 1 operatively connected to the proximal (12) and the distal (14) brace structures to impart movement to the limb of the user;

wherein the housing (22) is connected to the proximal (12) brace structure and the torque transfer output (38) is connected to the distal (14) brace structure.

16. The actuated orthothic device (10) of claim 15, wherein the transmission output (40) is operatively connected between the transmission input (34) and the gear reduction mechanism (36) through an opening of the second housing element (22b).

17. The actuated orthothic device (10) of claim 15, further comprising conical roller bearings (44) positioned between the center shaft (42) and the first housing element (22a).

18. The actuated orthothic device (10) of claim 15, wherein the center shaft (42) comprises a threaded portion (45) screwed into the torque transfer output (38) and a non-threaded portion (46) press-fitted within the torque transfer output (38).

19. The actuated orthothic device (10) of claim 15, wherein the transmission input (34) is a wave generator, the gear reduction mechanism (36) is a circular spline and the transmission output (40) is a flex spline forming a harmonic drive.

20. The actuated orthothic device (10) of claim 15, further comprising a torque limiting assembly (50) comprising:

a brake pad (62);

a band (52) connected at a first end to a first end of the brake pad (62); and a cam (56) linking a second end of the band (52) to a second end of the brake pad (62);

wherein the brake pad (62) and the band (52) are connected to the housing assembly (22) and positioned around the torque transfer output (38), whereby the positioning of the cam (56) in a first position frictionally engages the brake pad (62) and the band (52) with the torque transfer output (38), and positioning of the cam (56) in a second position disengages the brake pad (62) and the band (52) with the torque transfer output (38).

* * * * *